(12) United States Patent
Quaghebeur

(10) Patent No.: US 8,545,863 B2
(45) Date of Patent: Oct. 1, 2013

(54) INSECTICIDES FOR AGRICULTURAL AND HORTICULTURAL CROPS

(75) Inventor: Koen Quaghebeur, Wilderen (BE)

(73) Assignee: Globachem, Wilderen (BE)

( * ) Notice: Subject to any disclaimer, the term of this patent is extended or adjusted under 35 U.S.C. 154(b) by 0 days.

(21) Appl. No.: 13/318,875

(22) PCT Filed: May 4, 2010

(86) PCT No.: PCT/IB2010/051951
§ 371 (c)(1),
(2), (4) Date: Nov. 4, 2011

(87) PCT Pub. No.: WO2010/128456
PCT Pub. Date: Nov. 11, 2010

(65) Prior Publication Data
US 2012/0045527 A1 Feb. 23, 2012

(30) Foreign Application Priority Data
Jun. 5, 2009 (BE) .................................. 2009/0281

(51) Int. Cl.
*A01N 25/32* (2006.01)
*A01N 25/02* (2006.01)
*A01N 25/12* (2006.01)
*A01N 59/00* (2006.01)

(52) U.S. Cl.
USPC ........... 424/406; 424/405; 424/407; 424/409; 424/421; 424/715; 424/716; 424/717

(58) Field of Classification Search
None
See application file for complete search history.

(56) References Cited

U.S. PATENT DOCUMENTS

| | | |
|---|---|---|
| 5,342,630 A | 8/1994 | Jones |
| 5,739,172 A | 4/1998 | Jones |
| 2006/0040031 A1 | 2/2006 | Pascal et al. |

FOREIGN PATENT DOCUMENTS

| | | |
|---|---|---|
| JP | 5039206 | 2/1993 |
| WO | WO 9400982 | 1/1994 |
| WO | WO 9838867 | 9/1998 |
| WO | WO 2004/056184 | 7/2004 |

*Primary Examiner* — Neil Levy
(74) *Attorney, Agent, or Firm* — Jerold I. Schneider; Schneider Rothman IP Law Group

(57) ABSTRACT

Controlling insects of the superfamily of the Psylloidea in horticultural and/or agricultural crops, by using bicarbonate and carbonate salts.

17 Claims, No Drawings

INSECTICIDES FOR AGRICULTURAL AND HORTICULTURAL CROPS

CROSS-REFERENCE TO RELATED APPLICATIONS

This application is the entry into the United States of PCT Application Number PCT/IB2010/051951 filed May 4, 2010 and claims priority from Belgian Patent Application Number 2009/0281 filed May 6, 2009, the entirety of each of which are hereby incorporated by reference.

The invention relates to the control of insects of the superfamily of the Psylloidea in agricultural and horticultural crops, by using bicarbonate and/or carbonate salts.

BACKGROUND OF THE INVENTION

The use of bicarbonate and phosphate salts for the protection of agricultural and horticultural crops is well known. The most well known examples are potassium bicarbonate, sodium bicarbonate, ammonium bicarbonate and potassium phosphate, which are used on a large scale, especially in the US, for the control of fungal diseases.

A broad overview of the application of bicarbonate salts as fungicides is described in 'Control of apple scab (*Venturia inaequalis*) with bicarbonate salts under controlled environment', L. Jamar, B. Lefrancq & M. Lateur; Journal of Plant Diseases and Protection, 114 (5), 221-227, 2007, ISSN 1861-3829. Although the use of bicarbonate salts as an additive in food products is known, the application in controlling plant diseases has been limited. Bicarbonates have proven their activity in the control of a broad range of fungi, amongst others fungi that occur on food products, and in controlling plant pathogens. The activity of sodium bicarbonate in the control of mildew on cucumber is described, adding of surfactants seems to improve the activity against green fungus on citrus. It is explained that calcium hydroxide is capable of preventing the germination of spores and killing the spore sacks (asci) of apple scab (*V. inequalis*) in a concentration of 4.3 g/l. Potassium bicarbonate seems to be effective in decreasing fruit and leaf scab. The use of sodium bicarbonate as such or in combination with a reduced dose of tebuconazole for controlling apple scab in practical circumstances is mentioned. Besides this, other fungal diseases such as mildew, *Alternaria, Anthracnose, Botrytis*, . . . are described. Also the activity of watery solutions of bicarbonates mixed with vegetable or mineral oils in the control of apple scab is discussed.

The exact mechanism of how these salts operate is however not yet known. Different theories are described in which it is accepted that the salts cause a change in the pH of the leaf surface, or cause a damage of the cell wall membrane of the fungal spores as a result of which the spores dry out and die, or cause a disequilibrium between the K- or N-ions in the fungal cells as a result of which the cell wall bursts open.

The use of carbonate salts and further also phosphate salts as insecticides is also mentioned in a number of different publications.

JP 5039206 describes the use of a water-soluble powder of carbonates, bicarbonates, phosphates and sulphates for controlling aphidoidea such as aphids and acarina such as mites and ticks.

In the "Pakistan Journal of Botany", vol. 35, nr. 5, 2003 the use of $KH_2PO_4$ is described for controlling *Bemisia tabaci* and white flies.

In "Turkiye Entomoloji Dergisi" vol. 26, nr. 2, September 2002, the use of sodium bicarbonate is described for controlling aphids, white flies, and red spider mites in greenhouses.

In the "New Zealand Journal of Crop and Horticultural Science" vol. 27, nr. 2, the use of sodium bicarbonate is described for controlling larvae of *Epiphyas postvittana* Walker.

The "Queensland Journal of Agricultural and Animal Sciences", 1969, 26 (1), 83-8 describes the use of a white mixture of oil, soap and disodium carbonate for controlling white lice (*Unaspis citri*) and the Maori mite (*Phyllocoptrutua oleivora*).

WO 2004/056184 A1 describes the use of a powder comprising 40% wt. of sodium bicarbonate for use as an insecticide, more specifically as an acaricide and also as a fungicide in storage rooms for cereals, such as for example silos.

WO 94/00982 describes a pesticide composition comprising an inorganic salt chosen from alkali metal and ammonium bicarbonates, and an ingredient chosen from C8-C22 fatty acids, and salts thereof. This pesticide is described for use as a fungicide, herbicide and insecticide, without mentioning specific species of harmful organisms. The composition can be used for agricultural and horticultural applications, and as a shampoo for pets.

WO 89/10693 describes a method for protecting plants against phytophagous arthropods whereby a watery solution is applied, on the plant, of a composition comprising a monocarboxylic acid with 8-20 C-atoms, or salts thereof, with an agent for sequestering metal ions. As such an agent, phosphate salts are mentioned. This method is described against for example mites, aphids and white flies.

None of the previous publications however describes the use of the respective compositions comprising carbonate- or phosphate salts for controlling insects of the superfamily of the Psylloidea. Nonetheless, insects of this family, such as Pear Psylla, are an important threat for a great number of crops. Moreover, many known pesticides often have a minor or insufficient effect with respect to insects of this family.

EP 0322583 A1 describes an insecticide composition for controlling Pear Psylla, wherein the composition comprises an alkali-metal dioctyl-sulpho-succinate as an active ingredient. Besides this, the composition comprises a salt mixture with a buffering effect. As a salt mixture with a buffering effect, amongst others a phosphate buffer, a phthalate buffer, a citrate/phosphate buffer and a tartrate/phosphate buffer are mentioned.

WO 98/38867 describes a method for controlling arthropods whereby a certain quantity of a particle-shaped material is applied chosen from a large group of amongst other calcinated kaolins, hydrophobic calcinated kaolins, and hydrophobic calcium carbonates. This method is described for a large number of arthropods, such as insects, mites and spiders. More specifically, this method can be used against crawling, jumping, or flying arthropods. In example III, Pear Psylla is mentioned. The method relates to a physical plant protection product. Hereby the particle-shaped components are not soluble in water, as a result of which they do not control the arthropods mentioned as an active ingredient. By creating an environment containing these particle-shaped materials, a hostile environment for the arthropods is created, as a result of which these will be repelled such that they will not feed, and will not lay eggs. There is however no chemical interaction between the arthropods and the particle-shaped material, as a result of which they are not killed in a direct manner.

The compositions and methods described here above describe the control of insects of the superfamily of the Psylloidea, but offer an insufficient effectiveness in this control.

Other existing chemical insecticides with a broader action range which for example exert an altering function in the insect metabolism, have an insufficient effectiveness against insects of the superfamily of the Psylloidea, and are moreover often harmful for humans and the environment.

Given that lots of agricultural and horticultural products, more specifically seed fruit, for example apples and pears, are intended for both direct consumption by humans and animals whereby often not only the fruit pulp but also the outer peel is consumed, but which are also consumed as processed or prepared products, there is a need for a means for effectively controlling insects of the superfamily of the Psylloidea, which means has a low toxicity for the consumer and a low ecotoxicity and is more efficient than the existing pesticides for Psylloidea. It is after all also known that some insecticides and fungicides which are applied onto the peel do protrude into the pulp to a certain extent and often can not entirely or unsufficiently be removed from the peel by washing. Moreover there is a need for such a pesticide in which the risk for the development of resistance by the insects and parasites is strongly decreased.

DESCRIPTION OF THE INVENTION

It is the goal of the present invention to completely or partially solve the predescribed problems.

This is accomplished according to the present invention by using a water-soluble form of a salt of an anion chosen from the group of a bicarbonate, carbonate or a mixture of these salts as an active ingredient for the control of insects of the superfamily of the Psylloidea in horticultural and/or agricultural crops.

Preferably the more common salts of these anions which also show good water solubility are used as an active ingredient, especially carbonates and bicarbonates of Na, K or ammonium, or a mixture of two or more of these salts. Carbonates which are preferred are carbonates of sodium or potassium or a mixture thereof. Preferably potassium bicarbonate is used. The good water solubility guarantees an optimal uptake of the active ingredient by the insect.

Surprisingly the inventor has found that the listed bicarbonate and carbonate salts show an excellent action as an insecticide against insects of the superfamily of the Psylloidea, in a broad range of agricultural and horticultural crops, without causing harm to the crops. Where the usual insecticides bring the disadvantage of their toxicity, this problem does not occur with the active ingredient used in this invention.

Preferably the listed carbonate and bicarbonate salts are used for controlling insects of the family of the Psyllidae, more preferably for controlling Pear Psylla (Psylla pyri, Psylla pyricola).

Other harmful species of the superfamily of the Psylloidea which can be controlled with the current invention are for example Psylla mall, Trioza aguacate, Trioza apicalis, Cacopsylla pyrisuga, Ctenarytaina eucalypti, Cacopsylla buxi, Psyllopsis discrepans, etc.

Another important problem which occurs with the commonly used insecticides is that the insects develop a resistance for the insecticide as a result of which the activity decreases and the need for developing and using other products arises. The activity of the known insecticides is primarily directed to influencing the metabolic system of the parasite, against which resistance develops.

The inventors have now found that the risk for the development of resistance against the active ingredients of this invention is negligible. Moreover the listed active ingredients are not only active against insects from the superfamily of the Psylloidea, but also against their larvae, eggs and nits, as a result of which the risk for a revival of the pest is reduced. As such, while using the composition of the present invention for controlling Peach Psylla in pear trees, it was noticed that two spray treatments of 3 kg/hectare with an interval of two weeks were sufficient to reduce the egg-laying of Peach Psylla by 90%. It was found that also young larvae were killed by spraying the pear trees with the composition of the present invention. Repeated sprayings seemed to be capable of keeping the parcel nearly free of Pear Psylla.

Without being restricted by this theory, the inventor assumes that the activity of the composition of this invention is due to an irreversible fysico-chemical effect that is caused in insects of the superfamily of the Psylloidea, as a result of which they die. The development of resistance against fysicochemical effects has until now hardly been observed and this is an important advantage, given that this offers a guarantee that the product will maintain its activity for a long time during years.

De listed salts offer the advantage that they are not only capable of controlling insects of the superfamily of the Psylloidea, but that they are also capable of controlling diseases associated with these insects.

The active ingredient of the present invention is suitable for use as an insecticide for controlling insects of the superfamily of the Psylloidea in a large group of agricultural and horticultural crops, in all growing stages of the plants.

For example, the active ingredient of the present invention is suitable for use as an insecticide on fruit trees, pit fruit, and the blossoms thereof. Preferably the horticultural and/or agricultural crops are fruit trees, more preferably the horticultural and/or agricultural crops are pear trees. An optimal result is achieved in the application of controlling Pear Psylla in pears.

An additional advantage offered by the prescribed active ingredients is that they show a minor toxicity for humans and animals, that they are natural products which often play a crucial part in the functioning of an organism. They also occur in the soil, are used in lots of food products for humans and animals and have a very good toxicological profile.

The composition of this invention, more specifically bicarbonate and carbonate salts can be used in several formulations, but is preferably applied as a concentrated product in a concentration of 80-100%, preferably as a formulation chosen from an at least partially or completely crystalline powder, powder, granulate, suspension concentrate, emulsifiable concentrate of water-soluble concentrate. The person skilled in the art of controlling parasites in agriculture and horticulture is familiar with the use of such formulations and is capable of preparing such formulations. Typical formulation aids are inert additives (example: kaolin or China clay), solvents, thinners, dispersants and other ingredients.

As such it is known by the person skilled in the art that by using a spraying powder in water, a uniform dispersable formulation is obtained by use of a thinner, a dispersant and/or a wetting agent. Suitable wetting agents are for example ethoxylated polyoxy alkylphenoles, poly-ethoxylated fatty alcohols or fatty acidic amines, fatty alcohols, polyglycol ethersulfates, alkane sulfonates. Examples of suitable dispersants are sodium lignine sulphonic acid, 2,2-dimethylmethane-6,6'-disulphonic acid sodium salt, dibutyl naphthalene sulfonic acid sodium salt or oleyl methyletauric acid sodium salt.

For the use of bicarbonate- or carbonate salts of the present invention, ethoxylated sorbitane esters and ethoxylated alcohols are particularly interesting. By adding these additives, the activity can be substantially increased.

Emulsifiable concentrates are prepared by dissolving the active ingredient in an organic solvent. Examples of suitable solvents are butanol, cyclohexane, dimethylformamide, xylene or other high boiling aromatics and hydrocarbons. Possibly one or more emulsifiers can be used, which are usually applied in formulating sprayable or atomizable formulations in agricultural applications. Examples of suitable emulsifiers are calcium salts of alkylaryl sulphonates, for example calcium dodecyl benzene sulphonate, non-ionic emulsifiers such as fatty acid polyglycol esters, alkylaryl polyglycol ethers, fatty acid alcohol polyglycol ethers, propyleneoxide-ethylene oxide condensates such as: block polymers, alkyl polyethers, sorbitan fatty acid ester, polyoxy ethylene sorbitan fatty acid ester or polyoxyethylene sorbitan esters.

The composition preferably also comprises an effective quantity of a protection agent against decomposition under the influence of UV and visible light. Preferably, oxybenzone is used thereto, although other protection agents known by the person killed in the art can also be used.

The formulation according to this invention further preferably comprises one or more surfactants.

Formulations in the form of a granulate can be produced by using the active ingredient as such or by applying the active ingredient onto an inert carrier, for example by atomization, by adding a compatibiliser which increases the affinity of the active ingredient for the carrier such as a polyvinyl alcohol, a sodium salt of a polyacrylic acid, but any other technique known by the person skilled in the art can also be used. The surface of the carrier can also be treated with mineral oils. Examples of suitable carriers are sand, kaolin and inert granulates such as for example silica. Also the method used for producing fertilizer granulates is suitable for producing a granulate of the active ingredient of the present invention. If so desired, the active ingredient can be granulated together with one or more fertilizers.

Besides the previously mentioned active ingredients, the formulation of the active ingredient can also comprise the usual adhesives, humidifiers, dispersants, emulsifiers, impregnating agents and/or solvents as well as fillers or inert materials.

Also preferably one or more adjuvants are added to the formulation. Preferably these adjuvants are chosen from the group of glycerol and glycerol esters.

These adjuvants increase the biological activity of the active ingredient, as a result of which the quantity of active ingredient which has to be applied on the plants, can be decreased.

Examples of glycerol esters which can be used as an adjuvant are glycerol esters of frequently occurring fatty acids, for example glycerol mono-oleate, glycerol trioleate, glycerol monostearate, glycerol triacetate, etc.

The formulation of the present invention is for use, preferably diluted in an appropriate manner, preferably diluted with water to a watery solution in case of spraying powders, water-soluble concentrates, emulsion concentrates, dispersions and in water dispersable granulates.

The formulation of the present invention can be applied onto the agricultural and horticultural crops to be treated in any way considered suitable by the person skilled in the art, but is preferably applied by spraying or atomizing of a water-based formulation. Thereto a quantity of the powder or granulate is dissolved in water and atomized, whereby the concentration of the active ingredient is chosen such that 1-10 kg of active ingredient is applied per hectare of land area, preferably 2-6 kg per hectare of land area.

The formulation of the present invention can be applied onto the soil onto which the agricultural and horticultural crops are grown, but also onto the stem, the leaf and the fruits of the crops to be treated.

The invention further relates to a method for controlling insects of the superfamily of the Psylloidea whereby a formulation is applied onto agricultural and/or horticultural products which comprises as an active ingredient a salt of an anion chosen from the group of a bicarbonate, carbonate or a mixture of these salts.

The active ingredient is preferably dosed in a quantity corresponding to 1-10 kg per hectare of land area, more preferably in a quantity corresponding to 2-6 kg per hectare of land area to achieve an optimal killing of both the insects as the larvae.

Preferably the formulation is a crystalline or grounded, water-soluble product.

If one or more adjuvants, chosen from the group of glycerol and glycerol esters, are added, these are preferably dosed in a quantity corresponding to 0.1-3 kg per hectare of land area.

If so desired, the formulation may be a plant protection product which comprises a quantity of an active ingredient.

An optimal distribution over the crops to be treated is obtained by applying the active ingredient by spraying and/or atomization.

In a preferred embodiment of the method according to the present invention, the active ingredient is an at least partially crystalline powder.

I claim:

1. A method for controlling insects of the superfamily of the Psylloidea in horticultural and/or agricultural crops, by applying a watery solution of a salt of an anion chosen from the group of a bicarbonate, a carbonate and mixtures of these salts as an active ingredient, whereby the active ingredient is selected from bicarbonates and carbonates of Na, K and ammonium, and mixtures of at least two of these salts, and wherein the active ingredient is dosed in a quantity corresponding to 1-10 kg per hectare of land area.

2. The method according to claim 1, wherein the insects are chosen from the family of the Psyllidae.

3. The method according to claim 1, wherein the insect is Pear Psylla.

4. The method according to claim 1, wherein the active ingredient is selected from bicarbonates and carbonates of K and ammonium and mixtures of at least two of these salts.

5. The method according to claim 1, wherein the active ingredient is selected from bicarbonates of potassium and sodium and mixtures thereof.

6. The method according to claim 1, wherein the active ingredient is potassium bicarbonate.

7. The method according to claim 1 wherein a formulation is chosen from the group of a powder, a granulate, a suspension concentrate, an emulsifiable concentrate and a water-soluble concentrate whereby the formulation is diluted to the watery solution.

8. The method according to claim 7, wherein the formulation further comprises at least one surfactant.

9. The method according to claim 1, wherein the horticultural and/or agricultural crops are fruit trees.

10. The method according to claim 9, wherein the horticultural and/or agricultural crops are pear trees.

11. The method according to claim 1, wherein a formulation is chosen which is a crystalline or ground, water-soluble product whereby the formulation is diluted to the watery solution.

12. The method according to claim 1, wherein the watery solution further comprises at least one adjuvant chosen from the group of glycerol and glycerol esters.

13. The method according to claim 1, wherein the active ingredient is dosed in a quantity corresponding to 2-6 kg per hectare of land area.

14. The method according to claim 12 wherein the adjuvant is dosed in a quantity corresponding to 0.1-3 kg per hectare of land area.

15. The method according to claim 1, wherein a formulation is a plant protection product comprising a quantity of the active ingredient.

16. The method according to claim 1, wherein the active ingredient is applied by atomizing.

17. The method according to claim 1, wherein the active ingredient is an at least partially crystalline powder which is diluted to the watery solution.

* * * * *